(12) United States Patent
Sage et al.

(10) Patent No.: US 12,708,466 B2
(45) Date of Patent: Aug. 18, 2026

(54) ROBOTIC SURGICAL SYSTEM WITH CABLE CONNECTION DETECTION

(71) Applicant: Covidien LP, Mansfield, MA (US)

(72) Inventors: Lawrence A. Sage, Killingworth, CT (US); Edward J. Naclerio, Madison, CT (US)

(73) Assignee: Covidien LP, Mansfield, MA (US)

( * ) Notice: Subject to any disclaimer, the term of this patent is extended or adjusted under 35 U.S.C. 154(b) by 554 days.

(21) Appl. No.: 18/334,487

(22) Filed: Jun. 14, 2023

(65) Prior Publication Data

US 2024/0024050 A1 Jan. 25, 2024

Related U.S. Application Data

(60) Provisional application No. 63/390,658, filed on Jul. 20, 2022.

(51) Int. Cl.
*A61B 34/35* (2016.01)
*A61B 17/00* (2006.01)
*A61B 34/20* (2016.01)

(52) U.S. Cl.
CPC .............. *A61B 34/35* (2016.02); *A61B 17/00* (2013.01); *A61B 2017/00017* (2013.01); *A61B 2017/00115* (2013.01); *A61B 2034/2055* (2016.02)

(58) Field of Classification Search
CPC .................... A61B 34/35; A61B 17/00; A61B 2017/00017; A61B 2017/00115; A61B 2034/2055; A61B 34/37; A61B 90/98; A61B 2017/00477
USPC ........................................ 318/560, 567, 558
See application file for complete search history.

(56) References Cited

U.S. PATENT DOCUMENTS 6,132,368 A 10/2000 Cooper
6,206,903 B1 3/2001 Ramans
6,211,996 B1 * 4/2001 Fuse ........................ H03C 7/00 359/278
6,246,200 B1 6/2001 Blumenkranz et al.
6,312,435 B1 11/2001 Wallace et al.
6,331,181 B1 12/2001 Tierney et al.
6,394,998 B1 5/2002 Wallace et al.
6,424,885 B1 7/2002 Niemeyer et al.
(Continued)

FOREIGN PATENT DOCUMENTS

WO 2021158383 A1 8/2021

OTHER PUBLICATIONS

Extended European Search Report dated Nov. 29, 2023 (7 pages).

*Primary Examiner* — David Luo
(74) *Attorney, Agent, or Firm* — Carter, DeLuca & Farrell, LLP

(57) ABSTRACT

A surgical robotic system includes a control tower and a mobile cart. The control tower is configured to selectively output power and includes a frequency generator and a converter. The frequency generator is configured to generate an electrical frequency signal and the converter is configured to receive the electrical frequency signal and convert the electrical frequency signal to a first optical signal having a unique identifier frequency. The mobile cart is configured to receive the first optical signal from the control tower and includes an optical splice configured to loop the first optical signal back to the control tower as a second optical signal and deliver the first optical signal to a frequency monitor of the mobile cart.

20 Claims, 6 Drawing Sheets

(56) References Cited

U.S. PATENT DOCUMENTS 6,441,577 B2 8/2002 Blumenkranz et al.
6,459,926 B1 10/2002 Nowlin et al.
6,491,691 B1 12/2002 Morley et al.
6,491,701 B2 12/2002 Tierney et al.
6,493,608 B1 12/2002 Niemeyer
6,565,554 B1 5/2003 Niemeyer
6,645,196 B1 11/2003 Nixon et al.
6,659,939 B2 12/2003 Moll
6,671,581 B2 12/2003 Niemeyer et al.
6,676,684 B1 1/2004 Morley et al.
6,685,698 B2 2/2004 Morley et al.
6,699,235 B2 3/2004 Wallace et al.
6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban, III et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Tkowitz et al.
8,608,773 B2 12/2013 Tierney et al.
8,620,473 B2 12/2013 Diolaiti et al.
8,624,537 B2 1/2014 Nowlin et al.
8,634,957 B2 1/2014 Toth et al.
8,638,056 B2 1/2014 Goldberg et al.
8,638,057 B2 1/2014 Goldberg et al.
8,644,988 B2 2/2014 Prisco et al.
8,666,544 B2 3/2014 Moll et al.
8,668,638 B2 3/2014 Donhowe et al.
8,746,252 B2 6/2014 McGrogan et al.
8,749,189 B2 6/2014 Nowlin et al.
8,749,190 B2 6/2014 Nowlin et al.
8,758,352 B2 6/2014 Cooper et al.
8,761,930 B2 6/2014 Nixon
8,768,516 B2 7/2014 Diolaiti et al.
8,786,241 B2 7/2014 Nowlin et al.
8,790,243 B2 7/2014 Cooper et al.
8,808,164 B2 8/2014 Hoffman et al.
8,816,628 B2 8/2014 Nowlin et al.
8,821,480 B2 9/2014 Burbank
8,823,308 B2 9/2014 Nowlin et al.
8,827,989 B2 9/2014 Niemeyer
8,838,270 B2 9/2014 Druke et al.
8,852,174 B2 10/2014 Burbank
8,858,547 B2 10/2014 Brogna
8,862,268 B2 10/2014 Robinson et al.
8,864,751 B2 10/2014 Prisco et al.

(56) References Cited

U.S. PATENT DOCUMENTS 8,864,752 B2 10/2014 Diolaiti et al.
8,903,546 B2 12/2014 Diolaiti et al.
8,903,549 B2 12/2014 Itkowitz et al.
8,911,428 B2 12/2014 Cooper et al.
8,912,746 B2 12/2014 Reid et al.
8,944,070 B2 2/2015 Guthart
8,989,903 B2 3/2015 Weir et al.
9,002,518 B2 4/2015 Manzo
9,014,856 B2 4/2015 Manzo et al.
9,016,540 B2 4/2015 Whitman et al.
9,019,345 B2 4/2015 O'Grady et al.
9,043,027 B2 5/2015 Durant et al.
9,050,120 B2 6/2015 Swarup et al.
9,055,961 B2 6/2015 Manzo et al.
9,068,628 B2 6/2015 Solomon et al.
9,078,684 B2 7/2015 Williams
9,084,623 B2 7/2015 Gomez et al.
9,095,362 B2 8/2015 Dachs, II et al.
9,096,033 B2 8/2015 Holop et al.
9,101,381 B2 8/2015 Burbank et al.
9,113,877 B1 8/2015 Whitman et al.
9,138,284 B2 9/2015 Krom et al.
9,144,456 B2 9/2015 Rosa et al.
9,198,730 B2 12/2015 Prisco et al.
9,204,923 B2 12/2015 Manzo et al.
9,226,648 B2 1/2016 Saadat et al.
9,226,750 B2 1/2016 Weir et al.
9,226,761 B2 1/2016 Burbank
9,232,984 B2 1/2016 Guthart et al.
9,241,766 B2 1/2016 Duque et al.
9,241,767 B2 1/2016 Prisco et al.
9,241,769 B2 1/2016 Larkin et al.
9,259,275 B2 2/2016 Burbank
9,259,277 B2 2/2016 Rogers et al.
9,259,281 B2 2/2016 Griffiths et al.
9,259,282 B2 2/2016 Azizian et al.
9,261,172 B2 2/2016 Solomon et al.
9,265,567 B2 2/2016 Orban, III et al.
9,265,584 B2 2/2016 Itkowitz et al.
9,283,049 B2 3/2016 Diolaiti et al.
9,301,811 B2 4/2016 Goldberg et al.
9,314,307 B2 4/2016 Richmond et al.
9,317,651 B2 4/2016 Nixon
9,345,546 B2 5/2016 Toth et al.
9,393,017 B2 7/2016 Flanagan et al.
9,402,689 B2 8/2016 Prisco et al.
9,417,621 B2 8/2016 Diolaiti
9,424,303 B2 8/2016 Hoffman et al.
9,433,418 B2 9/2016 Whitman et al.
9,446,517 B2 9/2016 Burns et al.
9,452,020 B2 9/2016 Griffiths et al.
9,474,569 B2 10/2016 Manzo et al.
9,480,533 B2 11/2016 Devengenzo et al.
9,503,713 B2 11/2016 Zhao et al.
9,550,300 B2 1/2017 Danitz et al.
9,554,859 B2 1/2017 Nowlin et al.
9,566,124 B2 2/2017 Prisco et al.
9,579,164 B2 2/2017 Itkowitz et al.
9,585,641 B2 3/2017 Cooper et al.
9,615,883 B2 4/2017 Schena et al.
9,623,563 B2 4/2017 Nixon
9,623,902 B2 4/2017 Griffiths et al.
9,629,520 B2 4/2017 Diolaiti
9,662,177 B2 5/2017 Weir et al.
9,664,262 B2 5/2017 Donlon et al.
9,675,354 B2 6/2017 Weir et al.
9,687,312 B2 6/2017 Dachs, II et al.
9,700,334 B2 7/2017 Hinman et al.
9,718,190 B2 8/2017 Larkin et al.
9,730,719 B2 8/2017 Brisson et al.
9,737,199 B2 8/2017 Pistor et al.
9,795,446 B2 10/2017 DiMaio et al.
9,797,484 B2 10/2017 Solomon et al.
9,801,690 B2 10/2017 Larkin et al.
9,814,530 B2 11/2017 Weir et al.
9,814,536 B2 11/2017 Goldberg et al.
9,814,537 B2 11/2017 Itkowitz et al.
9,820,823 B2 11/2017 Richmond et al.
9,827,059 B2 11/2017 Robinson et al.
9,830,371 B2 11/2017 Hoffman et al.
9,839,481 B2 12/2017 Blumenkranz et al.
9,839,487 B2 12/2017 Dachs, II
9,850,994 B2 12/2017 Schena
9,855,102 B2 1/2018 Blumenkranz
9,855,107 B2 1/2018 Labonville et al.
9,872,737 B2 1/2018 Nixon
9,877,718 B2 1/2018 Weir et al.
9,883,920 B2 2/2018 Blumenkranz
9,888,974 B2 2/2018 Niemeyer
9,895,813 B2 2/2018 Blumenkranz et al.
9,901,408 B2 2/2018 Larkin
9,918,800 B2 3/2018 Itkowitz et al.
9,943,375 B2 4/2018 Blumenkranz et al.
9,948,852 B2 4/2018 Lilagan et al.
9,949,798 B2 4/2018 Weir
9,949,802 B2 4/2018 Cooper
9,952,107 B2 4/2018 Blumenkranz et al.
9,956,044 B2 5/2018 Gomez et al.
9,980,778 B2 5/2018 Ohline et al.
10,008,017 B2 6/2018 Itkowitz et al.
10,028,793 B2 7/2018 Griffiths et al.
10,033,308 B2 7/2018 Chaghajerdi et al.
10,034,719 B2 7/2018 Richmond et al.
10,052,167 B2 8/2018 Au et al.
10,072,972 B2 9/2018 Fusco et al.
10,085,811 B2 10/2018 Weir et al.
10,092,165 B2 10/2018 Power
10,092,344 B2 10/2018 Mohr et al.
10,123,844 B2 11/2018 Nowlin
10,188,469 B2 * 1/2019 Iida ...................... A61B 90/361
10,188,471 B2 1/2019 Brisson
10,201,390 B2 2/2019 Swarup et al.
10,213,202 B2 2/2019 Flanagan et al.
10,258,416 B2 4/2019 Mintz et al.
10,278,782 B2 5/2019 Jarc et al.
10,278,783 B2 5/2019 Itkowitz et al.
10,282,881 B2 5/2019 Itkowitz et al.
10,335,242 B2 7/2019 Devengenzo et al.
10,405,934 B2 9/2019 Prisco et al.
10,433,922 B2 10/2019 Itkowitz et al.
10,461,851 B1 * 10/2019 Zeng .................... H04B 10/503
10,464,219 B2 11/2019 Robinson et al.
10,485,621 B2 11/2019 Morrissette et al.
10,500,004 B2 12/2019 Hanuschik et al.
10,500,005 B2 12/2019 Weir et al.
10,500,007 B2 12/2019 Richmond et al.
10,502,912 B2 * 12/2019 Huegerich ........... H05K 5/0204
10,507,066 B2 12/2019 DiMaio et al.
10,510,267 B2 12/2019 Jarc et al.
10,524,871 B2 1/2020 Liao
10,548,459 B2 2/2020 Itkowitz et al.
10,575,909 B2 3/2020 Robinson et al.
10,592,529 B2 3/2020 Hoffman et al.
10,595,946 B2 3/2020 Nixon
10,838,816 B2 11/2020 Arroyo et al.
10,881,469 B2 1/2021 Robinson
10,881,473 B2 1/2021 Itkowitz et al.
10,898,188 B2 1/2021 Burbank
10,898,189 B2 1/2021 McDonald, II
10,905,506 B2 2/2021 Itkowitz et al.
10,912,544 B2 2/2021 Brisson et al.
10,912,619 B2 2/2021 Jarc et al.
10,918,387 B2 2/2021 Duque et al.
10,918,449 B2 2/2021 Solomon et al.
10,932,873 B2 3/2021 Griffiths et al.
10,932,877 B2 3/2021 Devengenzo et al.
10,939,969 B2 3/2021 Swarup et al.
10,939,973 B2 3/2021 DiMaio et al.
10,952,801 B2 3/2021 Miller et al.
10,965,933 B2 3/2021 Jarc
10,966,742 B2 4/2021 Rosa et al.
10,973,517 B2 4/2021 Wixey
10,973,519 B2 4/2021 Weir et al.
10,984,567 B2 4/2021 Itkowitz et al.

(56) References Cited

U.S. PATENT DOCUMENTS 10,993,773 B2 5/2021 Cooper et al.
10,993,775 B2 5/2021 Cooper et al.
11,000,331 B2 5/2021 Krom et al.
11,013,567 B2 5/2021 Wu et al.
11,020,138 B2 6/2021 Ragosta
11,020,191 B2 6/2021 Diolaiti et al.
11,020,193 B2 6/2021 Wixey et al.
11,026,755 B2 6/2021 Weir et al.
11,026,759 B2 6/2021 Donlon et al.
11,040,189 B2 6/2021 Vaders et al.
11,045,077 B2 6/2021 Stern et al.
11,045,274 B2 6/2021 Dachs et al.
11,058,501 B2 7/2021 Tokarchuk et al.
11,076,925 B2 8/2021 DiMaio et al.
11,090,119 B2 8/2021 Burbank
11,096,687 B2 8/2021 Flanagan et al.
11,098,803 B2 8/2021 Duque et al.
11,109,925 B2 9/2021 Cooper et al.
11,116,578 B2 9/2021 Hoffman et al.
11,129,683 B2 9/2021 Steger et al.
11,135,029 B2 10/2021 Suresh et al.
11,147,552 B2 10/2021 Burbank et al.
11,147,640 B2 10/2021 Jarc et al.
11,154,373 B2 10/2021 Abbott et al.
11,154,374 B2 10/2021 Hanuschik et al.
11,160,622 B2 11/2021 Goldberg et al.
11,160,625 B2 11/2021 Wixey et al.
11,161,243 B2 11/2021 Rabindran et al.
11,166,758 B2 11/2021 Mohr et al.
11,166,770 B2 11/2021 DiMaio et al.
11,166,773 B2 11/2021 Ragosta et al.
11,173,597 B2 11/2021 Rabindran et al.
11,185,378 B2 11/2021 Weir et al.
11,191,596 B2 12/2021 Thompson et al.
11,197,729 B2 12/2021 Thompson et al.
11,213,360 B2 1/2022 Hourtash et al.
11,221,863 B2 1/2022 Azizian et al.
11,234,700 B2 2/2022 Ragosta et al.
11,241,274 B2 2/2022 Vaders et al.
11,241,290 B2 2/2022 Waterbury et al.
11,259,870 B2 3/2022 DiMaio et al.
11,259,884 B2 3/2022 Burbank
11,272,993 B2 3/2022 Gomez et al.
11,272,994 B2 3/2022 Saraliev et al.
11,291,442 B2 4/2022 Wixey et al.
11,291,513 B2 4/2022 Manzo et al.
11,376,002 B2 7/2022 Shelton, IV et al.
11,376,098 B2 7/2022 Shelton, IV et al.
11,381,759 B2 7/2022 Zhao et al.
11,382,621 B2 7/2022 Scheib et al.
11,382,624 B2 7/2022 Harris et al.
11,382,625 B2 7/2022 Huitema et al.
11,382,626 B2 7/2022 Shelton, IV et al.
11,382,627 B2 7/2022 Huitema et al.
11,382,638 B2 7/2022 Harris et al.
11,382,644 B2 7/2022 Schoettgen et al.
11,389,160 B2 7/2022 Shelton, IV et al.
11,389,255 B2 7/2022 DiMaio et al.
11,399,906 B2 8/2022 Shelton, IV et al.
11,406,379 B2 8/2022 Hess et al.
11,410,259 B2 8/2022 Harris et al.
11,419,630 B2 8/2022 Yates et al.
11,424,027 B2 8/2022 Shelton, IV
11,432,888 B2 9/2022 Diolaiti et al.
11,432,893 B2 9/2022 Itkowitz et al.
11,432,895 B2 9/2022 Loh et al.
11,439,390 B2 9/2022 Patel et al.
11,439,391 B2 9/2022 Bruns et al.
11,468,791 B2 10/2022 Jarc et al.
11,471,155 B2 10/2022 Shelton, IV et al.
11,471,221 B2 10/2022 Zhao et al.
11,478,308 B2 10/2022 Hoffman et al.
11,490,977 B2 11/2022 Schena et al.
11,497,499 B2 11/2022 Shelton, IV et al.
11,504,119 B2 11/2022 Shelton, IV et al.
11,504,124 B2 11/2022 Patel et al.
11,510,743 B2 11/2022 Shelton, IV et al.
11,517,312 B2 12/2022 Wixey
11,517,325 B2 12/2022 Shelton, IV et al.
11,518,048 B2 12/2022 Saraliev et al.
11,756,672 B2 * 9/2023 Olson .................... G16H 30/20
2007/0009197 A1 1/2007 Poland et al.
2018/0228559 A1 8/2018 Brierton et al.
2019/0272369 A1 9/2019 Sanandajifar

* cited by examiner

ROBOTIC SURGICAL SYSTEM WITH CABLE CONNECTION DETECTION

CROSS-REFERENCE TO RELATED APPLICATION

This application claims the benefit of and priority to U.S. Provisional Patent Application No. 63/390,658, filed Jul. 20, 2022, the entire contents of which is incorporated by reference herein.

BACKGROUND

Surgical robotic systems generally include a surgeon console controlling one or more surgical robotic arms, each including a surgical instrument having an end effector (e.g., forceps or grasping instrument). In operation, the robotic arm is moved to a position over a patient and the surgical instrument is guided into a small incision via a surgical access port or a natural orifice of a patient to position the end effector at a work site within the patient's body. The surgeon console includes hand controllers which translate user input into movement of the surgical instrument and/or end effector.

Robotic arms and their corresponding surgical instruments are connected to an external power supply via a cable. There is a need for a system and method to verify that surgical instruments are properly connected to both the power supply and the robotic arm.

SUMMARY

According to one embodiment of the present disclosure, a method for selectively enabling power output is disclosed. The method includes generating a first optical signal having a unique identifier from a control tower, delivering the generated first optical signal from the control tower to an endpoint via an optical cable, and looping the first optical signal from the endpoint back to the control tower as a second optical signal. The method further includes determining whether a unique identifier of the delivered first optical signal is equal to an identifier of the second optical signal, and disabling power output from the control tower through the cable when it is determined that the identifier of the delivered first optical signal is not equal to the identifier of the second optical signal.

In an aspect, the endpoint is a mobile cart including a surgical instrument.

In an aspect, the method may further include enabling power output from the control tower through the cable when it is determined that the unique identifier of the delivered first optical signal is equal to the identifier of the second optical signal looped back from the endpoint.

In an aspect, the method may further include determining a connection point of the control tower based on the first optical signal.

In an aspect, disabling power output from the control tower may include preventing power from being generated.

According to another aspect of the present disclosure, a surgical robotic system includes a control tower and a mobile cart operably coupled to the control tower. The control tower is configured to selectively output power and includes a frequency generator and a converter. The frequency generator is configured to generate an electrical frequency signal and the converter is configured to receive the electrical frequency signal and convert the electrical frequency signal to a first optical signal having a unique identifier frequency. The mobile cart is configured to receive the first optical signal from the control tower and includes an optical splice configured to loop the first optical signal back to the control tower as a second optical signal and deliver the first optical signal to a frequency monitor of the mobile cart.

In an aspect, the control tower may further include a frequency monitor configured to receive the second optical signal from the optical splice and determine whether a frequency of the second optical signal received from the optical splice is equal to the frequency of the first optical signal converted by the converter of the control tower. Additionally or alternatively, the control tower may further include a converter configured to convert the second optical signal received from the optical splice to an electrical frequency signal. Additionally or alternatively, the control tower may be configured to prevent power generation when it is determined that the frequency of the second optical signal received from the optical splice is not equal to the frequency of the first optical signal converted by the converter of the control tower. Additionally or alternatively, the control tower may be configured to prevent power output to the mobile cart when it is determined that the frequency of the second optical signal received from the optical splice is not equal to the frequency of the first optical signal converted by the converter of the control tower. Additionally or alternatively, the control tower may be configured to enable power generation and power output to the mobile cart when it is determined that the frequency of the second optical signal received from the optical splice is equal to the frequency of the first optical signal converted by the converter of the control tower.

In an aspect, the mobile cart may be coupled to the control tower via a cable including at least one optical communication channel and at least one conductive power transmission channel. Additionally or alternatively, the cable may include two conductive power transmission channels separated by the at least one optical communication channel.

In an aspect, the frequency monitor of the mobile cart may be configured to determine to which tower connector of a plurality of tower connectors the mobile cart is coupled based on the first optical signal received from the control tower.

In an aspect, the frequency monitor of the mobile cart may be configured to detect a connection quality of the mobile cart to the control tower based on the first optical signal received from the control tower.

In an aspect, the mobile cart may further include a converter configured to convert the first optical signal received from the control tower to an electrical frequency signal and transmit the converted electrical frequency signal to the frequency monitor of the mobile cart.

According to another aspect of the present disclosure, a control tower of a surgical robotic system is provided. The control tower includes: a frequency generator configured to generate a first electrical frequency signal; a first converter configured to receive the first electrical frequency signal, convert the first electrical frequency signal to an optical signal, and deliver the optical signal to a mobile cart; a second converter configured to receive the optical signal back from a mobile cart and convert the received optical signal to a second electrical frequency signal; and a frequency monitor configured to receive the second electrical frequency signal and determine whether the second electrical frequency signal is equal to the first electrical frequency signal.

In an aspect, the control tower may be configured to prevent power generation or prevent power output when it is determined that the second electrical frequency signal is not equal to the first electrical frequency signal.

In an aspect, the control tower may be configured to enable power generation or enable power output when it is determined that the second electrical frequency signal is equal to the first electrical frequency signal.

In an aspect, the control tower further includes a tower connector including optical communication terminals and conductive power terminals configured to connect to a cable.

BRIEF DESCRIPTION OF THE DRAWINGS

Various embodiments of the present disclosure are described herein with reference to the drawings wherein.

DETAILED DESCRIPTION

Figure 1:
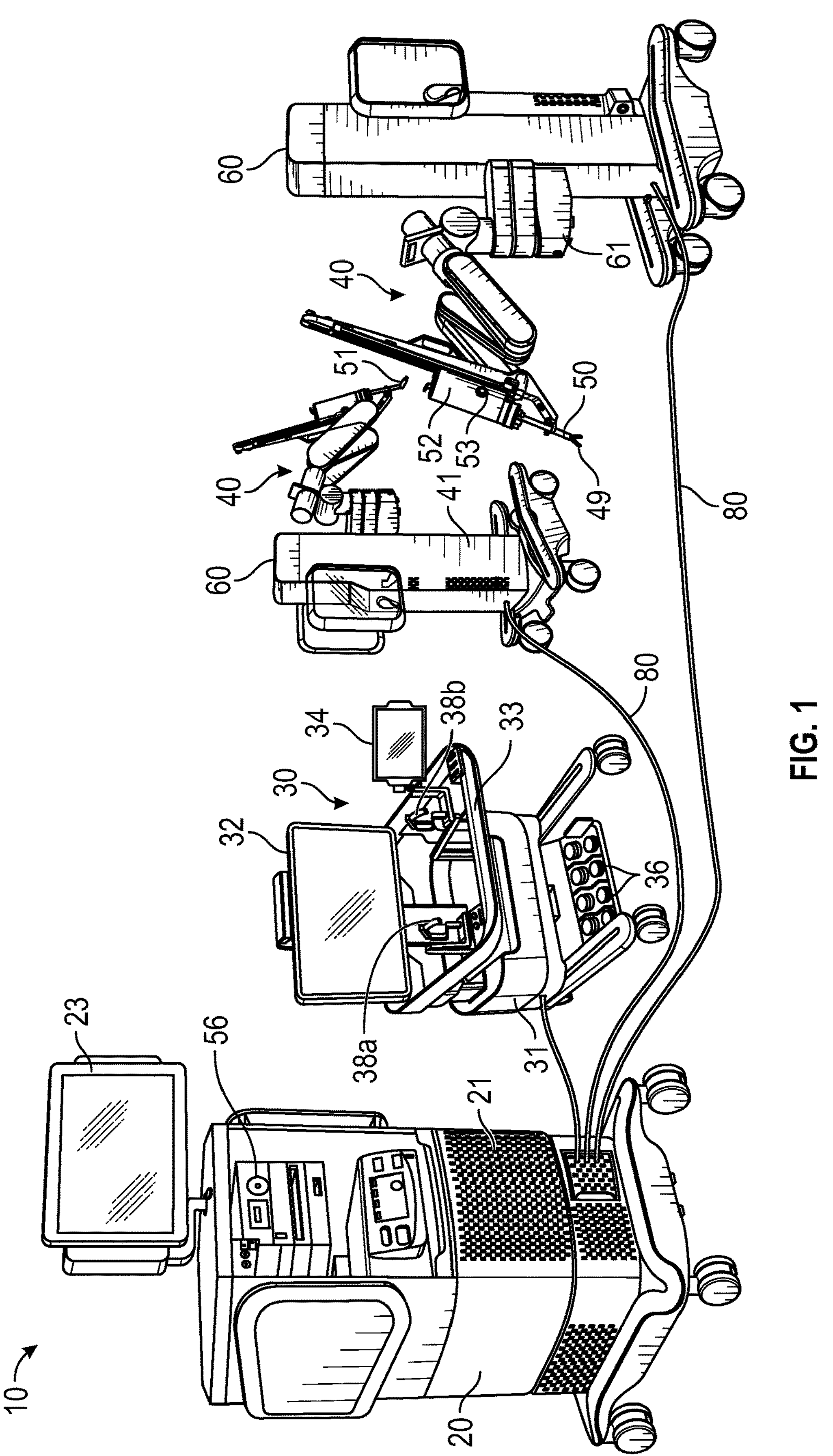
FIG. 1 is a schematic illustration of a surgical robotic system including a control tower, a console, and one or more surgical robotic arms each disposed on a mobile cart according to an embodiment of the present disclosure.

Embodiments of the presently disclosed surgical robotic system are described in detail with reference to the drawings, in which like reference numerals designate identical or corresponding elements in each of the several views.

As will be described in detail below, the present disclosure is directed to a surgical robotic system, which includes a surgeon console, a control tower, and one or more mobile carts having a surgical robotic arm coupled to a setup arm. The surgeon console receives user input through one or more interface devices, which are processed by the control tower as movement commands for moving the surgical robotic arm and an instrument and/or camera coupled thereto. Thus, the surgeon console enables teleoperation of the surgical arms and attached instruments/camera. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgeon console 30 and one or more mobile carts 60. Each of the mobile carts 60 includes a robotic arm having a surgical instrument 50 removably coupled thereto. The robotic arms 40 also couple to the mobile carts 60. The surgical robotic system 10 may include any number of mobile carts 60 and/or robotic arms 40. Each mobile cart 60 is coupled to the control tower 20 by a respective cable 80. Cable 80 is an optical hybrid cable including optical cables for data communications between the mobile cart 60 and the control tower 20 and conductive (e.g., copper) cables for power transmission from the control tower 20 to the mobile cart 60 and its components.

The disclosed control tower 20 includes a means to determine when a cable 80 has been connected between the control tower 20 and endpoints that require power from the control tower (e.g., mobile carts 60 and their connected components). The end points (e.g., mobile carts 60) may also read information from the control tower 20 via data communications through optical channels of the cable 80 to determine with which connection of the control tower 20 they are in contact.

According to the present disclosure, to enhance safety, all external cables 80 providing connections between parts of the surgical robotic system 10 that carry voltage, only have that voltage enabled (e.g., generated or output) when the cable 80 has been plugged in and has been detected to be properly connected. The surgical robotic system 10 according to the present disclosure provides the means for a plurality of cables 80 to be removably connected to a power supply (e.g., control tower 20).

As described above, the cable 80 utilizes optical cables for communications and conductive cables to provide power. The control tower 20 first determines that the cable 80 has been mated via an optical path prior to energizing the conductive path. This is accomplished by the control tower 20 generating an optical signal of specific frequency and injecting that optical signal into the cable 80 where the end point (e.g., mobile cart 60) receives the signal and loops back the signal to the control tower 20. The loopback is done passively via a spliced pair of optical fibers within the cable 80. Once the control tower 20 verifies that the signal has been looped back and is at the correct (e.g., matching) frequency, the control tower 20 makes the determination that the cable 80 is present and connected, then the control tower 20 enables power output to the endpoint (e.g., mobile cart 60).

For example, in support of four endpoints (e.g., four mobile carts 60), the control tower 20 generates four different optical frequencies, one for each endpoint. One of each of the frequencies is sent to just one of the endpoints (e.g., mobile cart 60) guaranteeing that each endpoint receives a different frequency. Based on that frequency, the endpoint can determine to which connection point it is mated on the control tower 20. Thus, an optical frequency generated by the control tower 20 is sent to each endpoint, loop-backed to the control tower 20 from the endpoint, verified for accuracy, and then used to determine when the cable 80 has been mated. That same optical frequency is monitored at the endpoint (e.g., mobile cart 60) and based on the frequency of that signal, used by the endpoint to determine its connection point and quality of connection into the control tower 20.

The control tower 20 generates and delivers different frequency signals to multiple individual mobile carts 60. Each port of the control tower 20 that connects to a mobile cart 60 has a different signal frequency. This allows each mobile cart 60 to determine which port of the control tower 20 it is attached to. Selecting the different frequency signals to be non-harmonically related also ensures the control tower 20 does not incorrectly identify which mobile cart 60 is attached to each individual port. Further, the use of a signal with different frequencies avoids issues with ambient light. That is, if the control tower 20 relied only on the presence of light, then if the cable were pointed at an illumination source that was sufficiently bright, then the control tower 20 might be fooled into thinking the cable was attached.

Rather than a frequency, the source, in this case, the control tower 20, could output a message consisting of serial data, such as through a UART (PC style serial port). Each mobile cart 60 would receive a different message. The mobile cart 60 would passively or actively loop the message back to the control tower 20. If the control tower 20 detects the message it sent, then the control tower 20 can positively assume that the mobile cart 60 is attached. If that message were different for each port on the control tower 20 that connected to a mobile cart 60, then the mobile cart 60 would know which port of the control tower 20 it was attached to. In aspects, other means may be utilized that rely on digital or analog communications, or possibly different light wavelengths (e.g., light colors).

The surgical instrument 50 is configured for use during minimally invasive surgical procedures. In embodiments, the surgical instrument 50 may be configured for open surgical procedures. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue. In yet further embodiments, the surgical instrument 50 may be a surgical clip applier including a pair of jaws configured apply a surgical clip onto tissue.

One of the robotic arms 40 may include an endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 and output the processed video stream.

The surgeon console 30 includes a first display 32, which displays a video feed of the surgical site provided by camera 51 of the surgical instrument 50 disposed on the robotic arm 40, and a second display 34, which displays a user interface for controlling the surgical robotic system 10. The first display 32 and second display 34 may be touchscreens allowing for displaying various graphical user inputs.

The surgeon console 30 also includes a plurality of user interface devices, such as foot pedals 36 and a pair of handle controllers 38*a* and 38*b* which are used by a user to remotely control robotic arms 40. The surgeon console further includes an armrest 33 used to support clinician's arms while operating the handle controllers 38*a* and 38*b*.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the handle controllers 38*a* and 38*b*. The foot pedals 36 may be used to enable and lock the handle controllers 38*a* and 38*b*, repositioning camera movement and electrosurgical activation/deactivation. In particular, the foot pedals 36 may be used to perform a clutching action on the handle controllers 38*a* and 38*b*. Clutching is initiated by pressing one of the foot pedals 36, which disconnects (i.e., prevents movement inputs) the handle controllers 38*a* and/or 38*b* from the robotic arm 40 and corresponding instrument 50 or camera 51 attached thereto. This allows the user to reposition the handle controllers 38*a* and 38*b* without moving the robotic arm(s) 40 and the instrument 50 and/or camera 51. This is useful when reaching control boundaries of the surgical space.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-1203 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
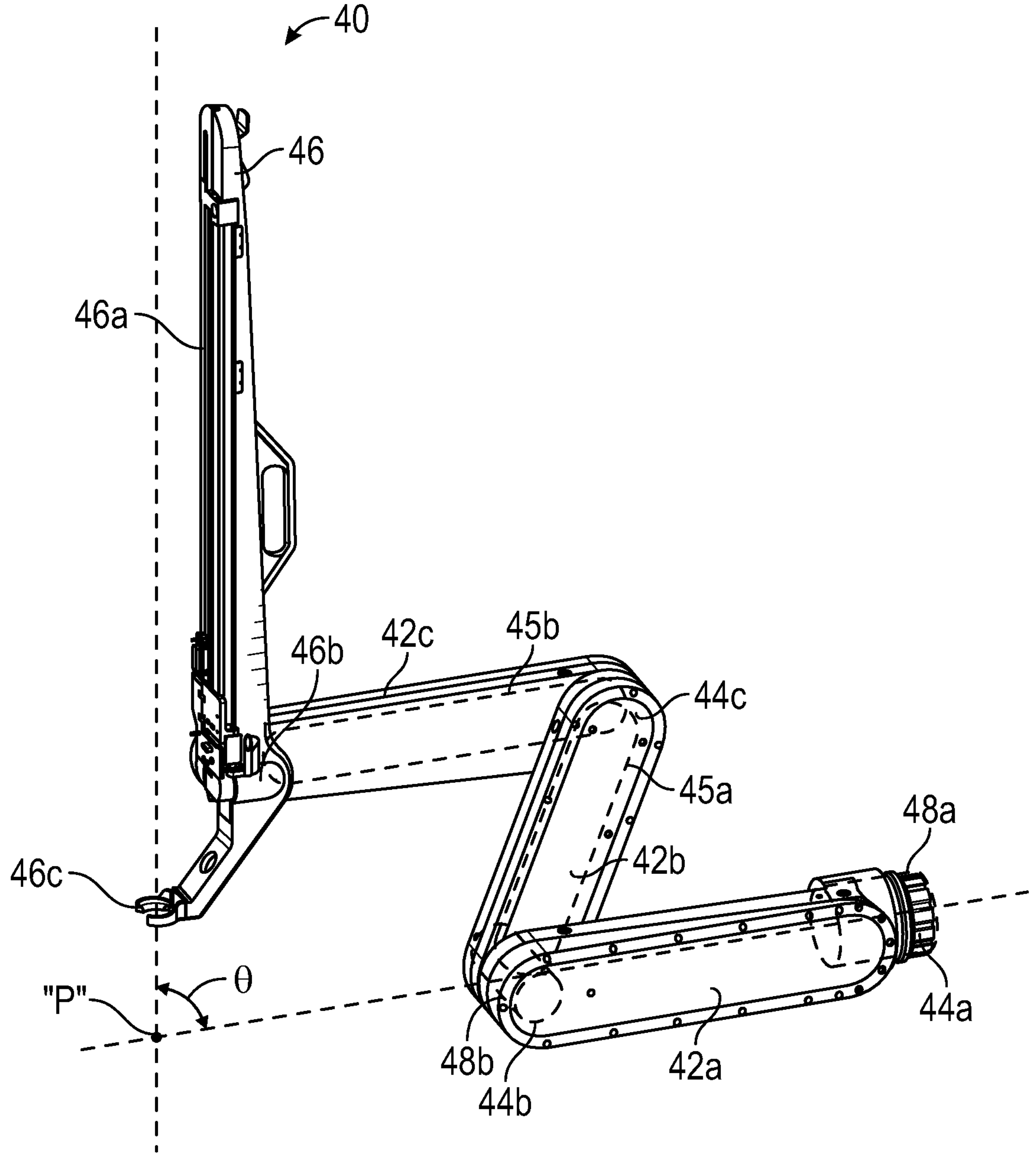
FIG. 2 is a perspective view of a surgical robotic arm of the surgical robotic system of FIG. 1 according to an embodiment of the present disclosure.
Figure 3:
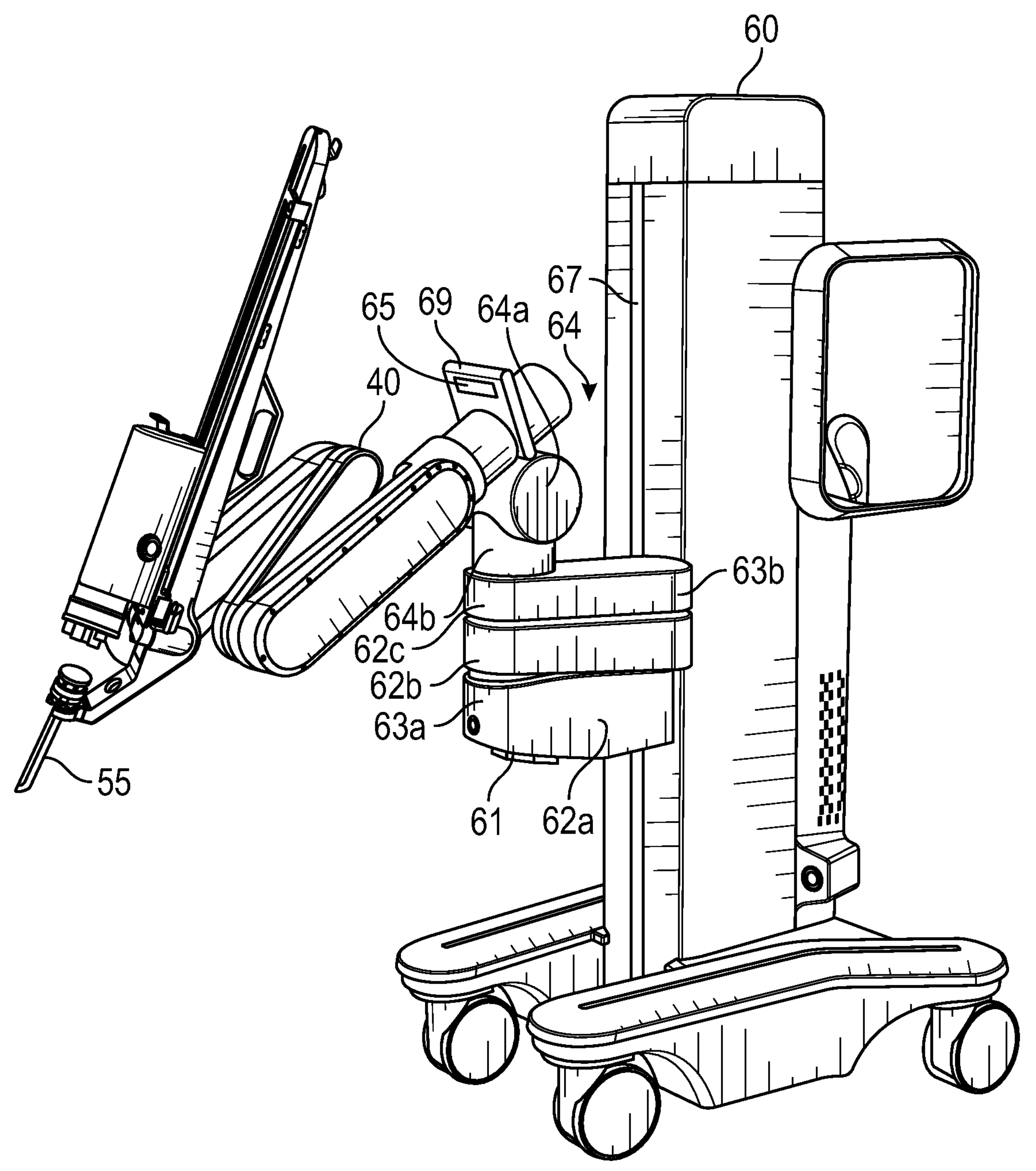
FIG. 3 is a perspective view of a mobile cart having a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. Other configurations of links and joints may be utilized as known by those skilled in the art. The joint 44*a* is configured to secure the robotic arm 40 to the mobile cart 60 and defines a first longitudinal axis. With reference to FIG. 3, the mobile cart 60 includes a lift 67 and a setup arm 61, which provides a base for mounting of the robotic arm 40. The lift 67 allows for vertical movement of the setup arm 61. The mobile cart 60 also includes a display 69 for displaying information pertaining to the robotic arm 40. In embodiments, the robotic arm 40 may include any type and/or number of joints.

The setup arm 61 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62*a*, 62*b*, 62*c* as well as the lift 67. In embodiments, the setup arm 61 may include any type and/or number of joints.

The third link 62*c* may include a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*b* via the belt 45*b*. Joint 44*c* may include a transfer case coupling the belts 45*a* and 45*b*, such that the actuator 48*b* is configured to rotate each of the links 42*b*, 42*c* and a holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. In other words, the pivot point "P" is a remote center of motion (RCM) for the robotic arm 40. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In embodiments, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the holder 46 defines a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components an end effector 49 of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During endoscopic procedures, the instrument 50 may be inserted through an endoscopic access port 55 (FIG. 3) held by the holder 46. The holder 46 also includes a port latch 46*c* for securing the access port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
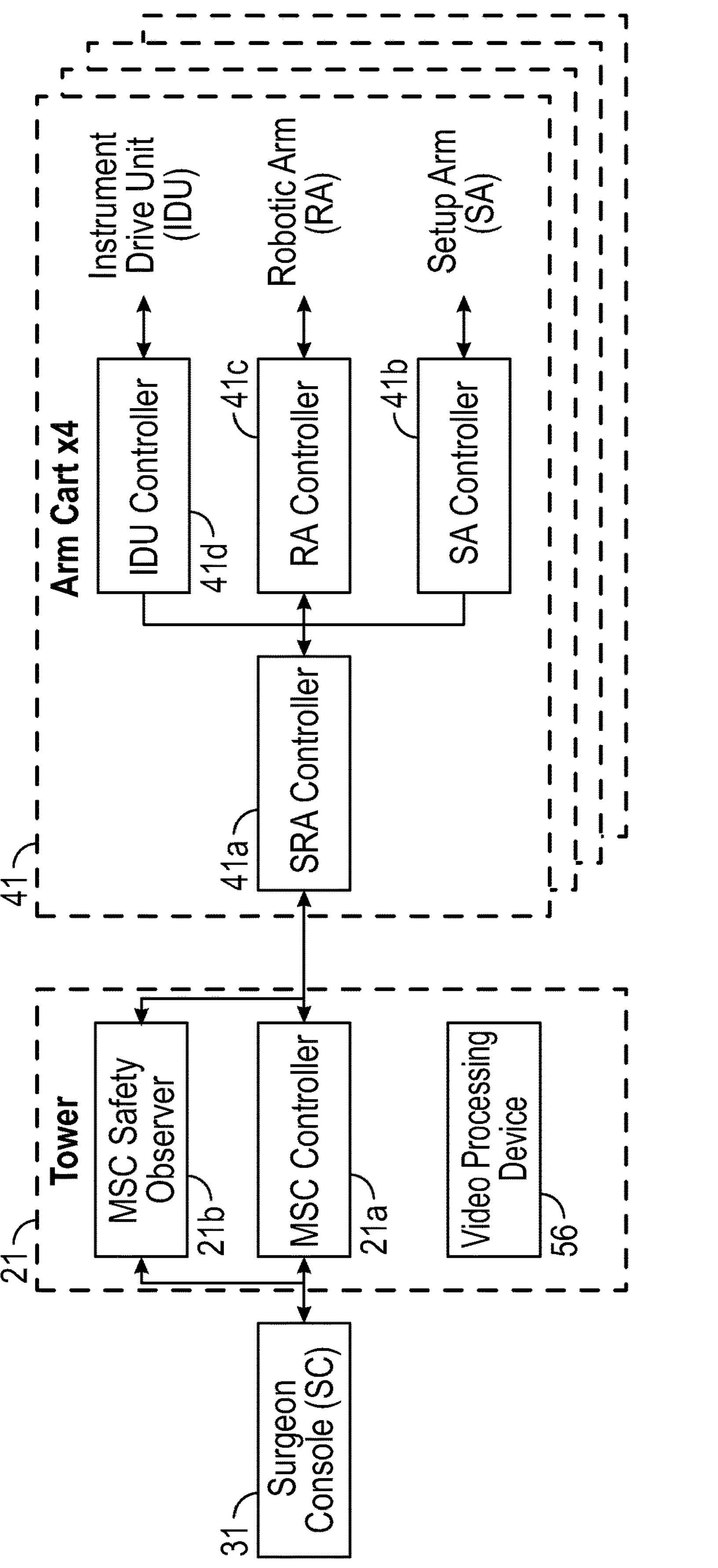
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system may include a plurality of controllers, which may be embodied in hardware and/or software. The computer 21 of the control tower 20 includes a controller 21*a* and safety observer 21*b*. The controller 21*a* receives data from the computer 31 of the surgeon console 30 about the current position and/or orientation of the handle controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the surgeon console 30 to provide haptic feedback through the handle controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the mobile cart 60, the robotic arm 40, and the IDU 52. The main cart controller 41*a* also communicates actual joint angles back to the controller 21*a*.

Each of joints 63*a* and 63*b* and the rotatable base 64 of the setup arm 61 are passive joints (i.e., no actuators are present therein) allowing for manual adjustment thereof by a user. The joints 63*a* and 63*b* and the rotatable base 64 include brakes that are disengaged by the user to configure the setup arm 61. The setup arm controller 41*b* monitors slippage of each of joints 63*a* and 63*b* and the rotatable base 64 of the setup arm 61, when brakes are engaged or can be freely moved by the operator when brakes are disengaged, but do not impact controls of other joints. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled in response to a pose of the handle controller controlling the robotic arm 40, e.g., the handle controller 38*a*, which is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controllers 38*a* may be embodied as a coordinate position and roll-pitch-yaw (RPY) orientation relative to a coordinate reference frame, which is fixed to the surgeon console 30. The desired pose of the instrument 50 is relative to a fixed frame on the robotic arm 40. The pose of the handle controller 38*a* is then scaled by a scaling function executed by the controller 21*a*. In embodiments, the coordinate position may be scaled down and the orientation may be scaled up by the scaling function. In addition, the controller 21*a* may also execute a clutching function, which disengages the handle controller 38*a* from the robotic arm 40. In particular, the controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Figure 5:
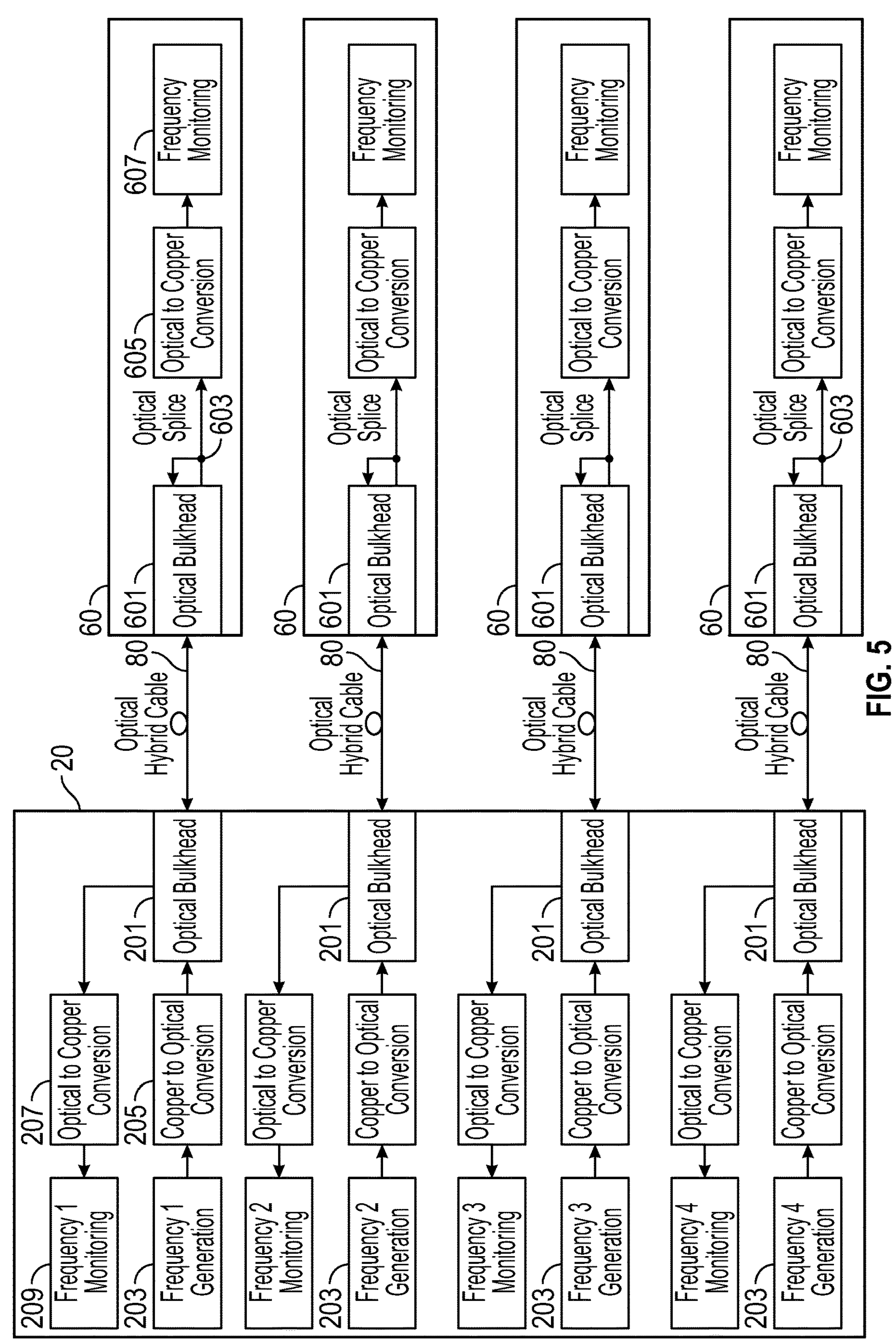
FIG. 5 is a schematic diagram of a control tower coupled to four mobile carts of the surgical robotic system according to an embodiment of the present disclosure.

Referring to FIG. 5, a control tower 20 is shown coupled to a plurality of mobile carts 60 via respective cables 80. Although FIG. 5 illustrates four mobile carts 60 coupled to the control tower 20, it is understood that any number of mobile carts 60, more or less than four, may be coupled to the control tower 20. One end of the cable 80 is configured to removably couple to a tower connector 201 of the control tower 20 and the other end of the cable 80 is configured to couple to a cart connector 601 of the mobile cart 60. As described above, the cable 80 is an optical hybrid cable including optical cables for data communications between the mobile cart 60 and the control tower 20 and conductive (e.g., copper) cables for power transmission from the control tower 20 to the mobile cart 60 and its components. Thus, each of the tower connector 201 and the cart connector 601 includes one or more optical communication channels and one or more conductive electrical communication channels (e.g., conductive power transmission channels). In aspects, each cable 80 includes at least two optical communications channels (e.g., for delivery and receipt of optical signals, respectively) and two conductive wires. In aspects, the two conductive wires of the cable 80 are separated from each other by the optical channel(s), thereby reducing interference therebetween.

The control tower 20 is configured to detect when a mobile cart 60 is coupled to the control tower 20 via the cable 80. After a proper connection between the control tower 20 and the mobile cart 60 is confirmed, the control tower 20 then enables the output of power for transmission of the power through the cable 80 from the control tower 20 to the mobile cart 60. Thus, power is not activated and/or output, and therefore not transmitted through the cable 80, until a proper connection of the cable 80 between the control tower 20 and the mobile cart 60 is confirmed.

The control tower 20 includes a frequency generator 203 operably coupled to the tower connector 201 via a copper to optical converter 205. The frequency generator 203 generates an electrical frequency signal which is converted into an optical signal by the copper to optical converter 205. The cable 80 transmits the optical signal from the tower connector 201 of the control tower 20 to the cart connector 601 of the mobile cart 60 via an optical delivery channel of the cable 80. The mobile cart 60 includes an optical splice 603 downstream of the cart connector 601. The optical slice 603 loops the optical signal back into the cart connector 601 for transmission of the optical signal back to the tower connector 201 of the control tower 20 via an optical receiver channel of the cable 80. Once the optical signal is looped back to the control tower 20, the optical signal is converted to an electrical frequency signal by an optical-to-electrical converter 207, that is operably coupled to the tower connector 201, which is then output to a frequency monitor 209.

Although frequency generator 203 is described as generating an electrical frequency signal and frequency monitor 209 is described as comparing electrical frequency signals, it is understood that frequency generator 203 may generate any unique identifier characteristic and frequency monitor 209 may compare any unique identifier characteristics and are not limited to signal frequencies.

The frequency monitor 209 is configured to compare the electrical frequency signal received from the optical-to-electrical converter 207 to the electrical frequency signal generated by the frequency generator 203 and determine whether the two are the same. If the electrical frequency signal received from the optical-to-electrical converter 207 is the same as the electrical frequency signal generated by the frequency generator 203, then the control tower 20 enables power output through the tower connector 201 for transmission through the connected cable 80 to the mobile cart 60, since the match in the frequencies confirms that the connection is proper. On the other hand, if the electrical frequency signal received from the optical-to-electrical converter 207 is not the same as the electrical frequency signal generated by the frequency generator 203, or of no electrical frequency signal is received from the optical-to-electrical converter 207, then the control tower 20 does not initiate power activation and thus, no power is output from, the tower connector 201.

In addition to looping the optical signal back to the control tower 20 from the optical splice 603, the optical signal is also transmitted from the optical splice 603 to an optical-to-electrical converter 605 of the mobile cart 60 for conversion of the optical signal to an electrical frequency signal. The electrical frequency signal is output from the optical-to-electrical converter 605 to a frequency monitor 607 of the mobile cart 60 so that the mobile cart 60 can also determine its connection to the control tower 20.

FIG. 5 illustrates connection between the control tower 20 and four mobile carts 60 via respective cables 80. The control tower 20 may include any number of tower connectors 201 for connecting to any number of the mobile carts 60 and other corresponding components (e.g., frequency generator 203, copper to optical converter 205, optical-to-electrical converter 207, and frequency monitor 209). Each frequency generator 203 may be configured to generate its own distinct electrical frequency signal, so that each of the mobile carts 60 coupled to the control tower receives a unique identifier signal (e.g., optical signal) having a different frequency. Thus, in the configuration illustrated in FIG. 5, where four mobile carts 60 are shown, the control tower 20 generates four signals at different optical frequencies. Each signal is sent to only one of the endpoints (e.g., just one of the mobile carts 60) guaranteeing that each endpoint (e.g., mobile cart receives a signal having a different frequency. Based on that frequency, the endpoint (e.g., mobile cart 60) determines to which tower connector 201 the mobile cart 60 is mated to on the control tower 20.

Figure 6:
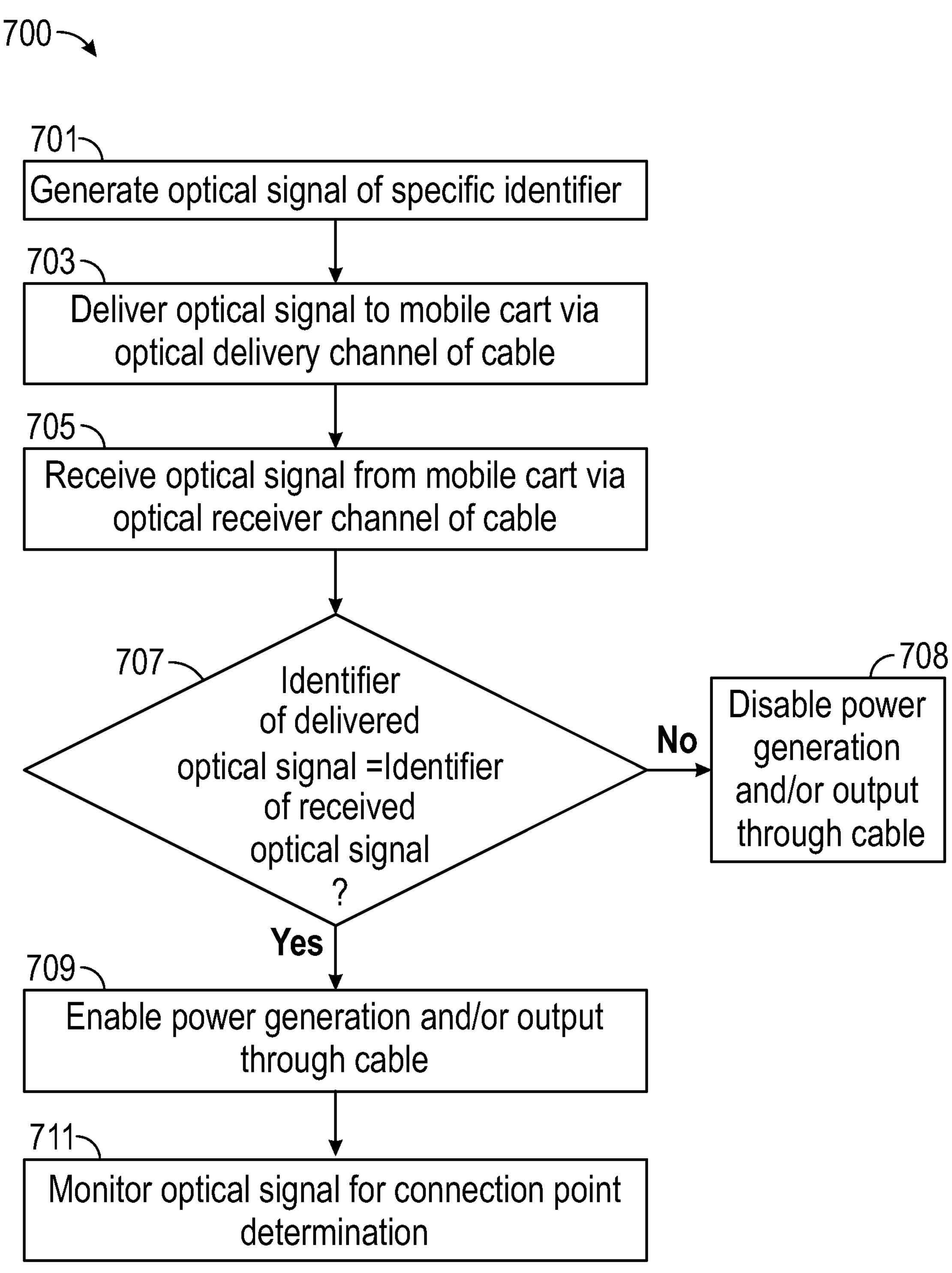
FIG. 6 is a flow chart of a method for confirming cable connections of the surgical robotic system and controlling power output according to an embodiment of the present disclosure.

FIG. 6 illustrates a method for enabling power output to an endpoint, such as a mobile cart 60 and its components, and is described as method 700. Method 700 may include some or all of the steps described and illustrated in FIG. 6, and the steps of method 700 may be carried out in any order not specifically illustrated or described. Although method 700 is described as being carried out by control tower 20 and mobile cart 60, it is understood that some or all of the steps of method 700 may be carried out by one or more of any of the components of surgical robotic system alone or in combination.

At step 701, the control tower 20 generates one or more optical signals having a unique identifier (e.g., a unique frequency, amplitude, etc.). In aspects, control tower 20 has multiple outputs (e.g., multiple tower connectors 201) for connecting to, and powering, multiple mobile carts 60. Therefore, step 701 may include generating multiple optical signals, each having a different identifier (e.g., unique frequency, amplitude, etc.) and each configured to be delivered through a different tower connector 201. In step 703, each optical signal generated in step 701 is delivered to a respective mobile cart 60 via the optical delivery channel of the cable 80.

As described above, once the optical signal is delivered to the mobile cart 60, the mobile cart 60 loops the optical signal back to the control tower 20 via the optical splice 603 in the mobile cart 60. Thus, in step 705 the control tower 20 receives the optical signal from the mobile cart 60 via the optical receiver channel of the cable 80.

In step 707, the control tower 20 compares the identifier (e.g., frequency, amplitude, etc.) of the optical signal delivered to the mobile cart 60 with the identifier (e.g., frequency, amplitude, etc.) of the optical signal received back from the mobile cart 60 and determines whether the two are equivalent. If the control tower 20 determines that the optical signal delivered to the mobile cart 60 is equal to the optical signal received from the mobile cart 60 (YES in step 707), then method 700 proceeds to step 709. On the other hand, if the control tower 20 determines that the optical signal delivered to the mobile cart 60 is not equal to the optical signal received from the mobile cart 60 (NO in step 707), then method 700 proceeds to step 708.

In step 708, the control tower 20 disables power output through the cable 80. Step 708 may be accomplished by preventing or disabling the control tower 20 from generating power to be output and/or by blocking power generated by the control tower 20 from being delivered from the control tower 20 (e.g., to cable 80). On the other hand, when the control tower 20 determines that the optical signal received from the mobile cart 60 is the same as the optical signal that was delivered to the mobile cart 60, then in step 709 the control tower 20 enables the generation of power and/or enables the output of generated power through the cable 80 to the mobile cart 60.

In step 711, the mobile cart 60 monitors the optical signal and, based on the unique identifier (e.g., frequency, amplitude, etc.) of the optical signal, determines to which tower connector 201 of the control tower 20 the mobile cart 60 is connected. Additionally, by monitoring the optical signal in step 611, the mobile cart 60 can determine whether the cable 80 has been disconnected from the control tower 20 (e.g., in aspects where the mobile cart 60 has a back-up power supply).

Using an optical frequency variant solution, or other unique identifier solution, for cable presence detection and mobile cart 60 identification may allow the system 10 to limit the number of copper connections in the cable used to connect the mobile cart 60 to the control tower 20 to the bare minimum in support of only power transfer. This minimizes the weight, flexibility, cost, and diameter of the cable 80. By limiting the number of copper connections, the end connectors of the cable 80 also remain smaller in diameter. Insertion and extraction forces of the cable 80 also remain smaller due to the minimization of friction caused by the copper connections. This solution may also allow the cable 80 to provide distances between conductors that enable one means of electrical protection (e.g., by separation of the electrical conductors by optical cables within the cable 80), as defined by IEC60601, which enhances electrical safety.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A method for selectively enabling power output comprising:

generating a first optical signal having a unique identifier from a control tower;

delivering the first optical signal from the control tower to an endpoint via an optical cable;

looping the first optical signal from the endpoint back to the control tower as a second optical signal;

determining whether the identifier of the first optical signal is equal to an identifier of the second optical signal; and disabling power output from the control tower through the cable when it is determined that the unique identifier of the delivered first optical signal is not equal to the identifier of the second optical signal.

2. The method according to claim 1, wherein the endpoint is a mobile cart including a surgical instrument.

3. The method according to claim 1, further comprising enabling power output from the control tower through the cable when it is determined that the unique identifier of the delivered first optical signal is equal to the identifier of the second optical signal.

4. The method according to claim 1, further comprising determining a connection point of the control tower based on the first optical signal.

5. The method according to claim 1, wherein disabling power output from the control tower includes preventing power from being generated.

6. A surgical robotic system comprising:

a control tower configured to selectively output power including:

a frequency generator configured to generate an electrical frequency signal having a unique identifier frequency; and a converter configured to receive the electrical frequency signal and convert the electrical frequency signal to a first optical signal; and a mobile cart configured to couple to the control tower and receive the first optical signal from the control tower, the mobile cart including:

an optical splice configured to loop the first optical signal back to the control tower as a second optical signal and deliver the first optical signal to a frequency monitor of the mobile cart.

7. The surgical robotic system according to claim 6, wherein the control tower further includes a frequency monitor configured to receive the second optical signal from the optical splice and determine whether a frequency of the second optical signal received from the optical splice is equal to the frequency of the first optical signal converted by the converter of the control tower.

8. The surgical robotic system according to claim 7, wherein the control tower further includes a converter configured to convert the second optical signal received from the optical splice to an electrical frequency signal.

9. The surgical robotic system according to claim 7, wherein the control tower is configured to prevent power generation when it is determined that the frequency of the second optical signal received from the optical splice is not equal to the frequency of the first optical signal converted by the converter of the control tower.

10. The surgical robotic system according to claim 7, wherein the control tower is configured to prevent power output to the mobile cart when it is determined that the frequency of the second optical signal received from the optical splice is not equal to the frequency of the first optical signal converted by the converter of the control tower.

11. The surgical robotic system according to claim 7, wherein the control tower is configured to enable power generation and power output to the mobile cart when it is determined that the frequency of the second optical signal received from the optical splice is equal to the frequency of the first optical signal converted by the converter of the control tower.

12. The surgical robotic system according to claim 6, wherein the mobile cart is coupled to the control tower via a cable including at least one optical communication channel and at least one conductive power transmission channel.

13. The surgical robotic system according to claim 12, wherein the cable includes two conductive power transmission channels separated by the at least one optical communication channel.

14. The surgical robotic system according to claim 6, wherein the frequency monitor of the mobile cart is configured to determine to which tower connector of a plurality of tower connectors of the control tower the mobile cart is coupled based on the first optical signal received from the control tower.

15. The surgical robotic system according to claim 6, wherein the frequency monitor of the mobile cart is configured to detect a connection quality of the mobile cart to the control tower based on the first optical signal received from the control tower.

16. The surgical robotic system according to claim 6, wherein the mobile cart further includes a converter configured to convert the first optical signal received from the control tower to an electrical frequency signal and transmit the converted electrical frequency signal to the frequency monitor of the mobile cart.

17. A control tower of a surgical robotic system, the control tower comprising:

a frequency generator configured to generate a first electrical frequency signal;

a first converter configured to receive the first electrical frequency signal, convert the first electrical frequency signal to an optical signal, and deliver the optical signal to a mobile cart;

a second converter configured to receive the optical signal back from a mobile cart and convert the received optical signal to a second electrical frequency signal; and a frequency monitor configured to receive the second electrical frequency signal and determine whether the second electrical frequency signal is equal to the first electrical frequency signal.

18. The control tower according to claim 17, wherein the control tower is configured to prevent power generation or prevent power output when it is determined that the second electrical frequency signal is not equal to the first electrical frequency signal.

19. The control tower according to claim 17, wherein the control tower is configured to enable power generation or enable power output when it is determined that the second electrical frequency signal is equal to the first electrical frequency signal.

20. The control tower according to claim 17, further comprising a tower connector including optical communication terminals and conductive power terminals configured to connect to a cable.

* * * * *